United States Patent [19]

Stillman

[11] 4,410,517

[45] Oct. 18, 1983

[54] VITAMIN E (TOCOPHEROL) COMPOSITIONS WHICH RESEMBLE PETROLATUM

[76] Inventor: Theodore Stillman, Box 63, Hardy, Ark. 72542

[21] Appl. No.: 290,157

[22] Filed: Aug. 5, 1981

Related U.S. Application Data

[63] Continuation of Ser. No. 151,627, May 20, 1980, abandoned.

[51] Int. Cl.$^3$ .................... A61K 35/78; A61K 31/355
[52] U.S. Cl. .................... 424/195; 424/284; 424/365; 251/11; 252/52 R
[58] Field of Search .................. 424/284, 195; 252/11, 252/52 R

[56] References Cited

U.S. PATENT DOCUMENTS

| | | | |
|---|---|---|---|
| 2,582,395 | 1/1952 | Rigby | 424/284 |
| 2,628,930 | 2/1953 | Zentner | 424/284 |
| 3,244,595 | 4/1966 | Feigh | 424/237 |

FOREIGN PATENT DOCUMENTS 629433 10/1961 Canada ................................ 424/284

OTHER PUBLICATIONS

Manufacturing Chemist & Aerosol News, Jun. 1979, p. 47.

*Primary Examiner*—Donald B. Moyer
*Attorney, Agent, or Firm*—Milton M. Field

[57] ABSTRACT

Compositions are disclosed which consist of appropriate quantities and types of glyceryl monostearate dissolved into appropriate quantities and types of vitamin E. Appropriate mixtures or solutions of glyceryl monostearate and vitamine E resemble Vaseline (petrolatum) and can be used as a substitute for Vaseline in all its areas of use. The result is hardened vitamin E (defined as a solution that contains over 50% vitamin E). The remainder of the solution contains glyeryl monostearate.

A third compound such as jojoba oil may be added to the above compositions. Other types of vegetable, or seed oils have been considered as an additive to the above compositions, but are not strongly recommended because of the dangers that are associated with rancid oils. Jojoba oil is the only oil that is compatible with the above solution and resistant to oxidation. Vegetable and seed oils are compatible but they also turn rancid. This invention deals only with solutions that contain at least 50% vitamin E in its total formulation as measured by weight. The concentrations of the ingredients will determine the effectiveness of the formulation as a substitute for Vaseline as a sexual lubricant.

2 Claims, No Drawings

VITAMIN E (TOCOPHEROL) COMPOSITIONS WHICH RESEMBLE PETROLATUM

This application is a continuation of prior U.S. application Ser. No. 151,627 filed May 20, 1980, now abandoned.

BACKGROUND OF THE INVENTION

1. Field of the Invention

This invention relates to vitamin E (tocopherol) compositions that resemble solid petrolatum (Vaseline) and can be used as a lubricant during sexual intercourse or applied to the skin in thick coatings. Since more than 50% of the resulting compositions will be vitamin E, the resulting compositions can still be called vitamin E. Thus, this invention hardens vitamin E into a substance that resembles solid petrolatum (Vaseline). The specific concentrations, the specific types of glyceryl monostearate, and the specific types of vitamin E, which will achieve the above objectives, are disclosed in this application.

2. Brief Description of Prior Art

Vitamin E and glyceryl monostearate have been combined in conjunction with other compounds, and other objectives. It has never before been realized that vitamin E, and glyceryl monostearate could form a solution which could be a substitute for petrolatum, or Vaseline. In fact, no one has pointed out that glyceryl monostearate, and vitamin E could be the only ingredients of a finished and saleable product.

More importantly, no one has accurately described the factors that would have to be considered in formulating such a product. This, there is no prior work in this field. However, glyceryl monostearate and vitamin E have been combined in other fields but always in conjunction with other ingredients. Zentner U.S. Pat. No. 2,628,930 teaches combining glyceryl monostearate and vitamin E along with a variety of other compounds in order to emulsify fat soluble vitamins. A solution that contains only vitamin E and glyceryl monostearate was not prepared or commented upon.

Brooks U.S. Pat. No. 3,253,992 was also primarily interested in preparing water emulsions and also used many other compounds in his formulations. Any of these compounds would have masked the potential of using solutions that contain only vitamin E and glyceryl monostearate.

Rigby U.S. Pat. No. 2,582,395 uses glyceryl monostearate and vitamin E. However, the vitamin E is in concentrations of less than 1%. In addition, his formulas have many other ingredients. Thus, he could not possibly describe solutions that only contain vitamin E and glyceryl monostearate. Nor did he comment on such a solution.

Hochberg U.S. Pat. No. 2,777,797 uses some type of glyceride to harden vitamin E. However, he was primarily concerned with achieving his change of state with flour. Thus, he failed to realize that a solution that contains only glyceryl monostearate and vitamin E could be useful by itself.

Tingstad Canadian Pat. No. 629,433 uses glyceryl monostearate to prepare ointments. However, his formulas contain less than 1% vitamin E. Thus, there is no way for him to describe the effect of glyceryl monostearate on solutions that contain only vitamin E.

Thus, no one has tried to prepare solutions that only contain vitamin E and glyceryl monostearate to be used as end products. In other words, no one has explored the ways and means of combining these two compounds in order to produce hardened vitamin E. Hardened vitamin E is defined as a product that has more than 50% vitamin E combined with glyceryl monostearate. This raises three questions:

1. What is the effect of various concentrations of glyceryl monostearate on the physical properties of the solution formed by dissolving glyceryl monostearate into vitamin E?

2. There are several different types of vitamin E and several different types of glyceryl monostearate. What is the effect of combining these different types on the physical properties of the solution formed by dissolving one into the other?

3. What is the effect of using more than one type of glyceryl monostearate on the physical properties of the solution formed by dissolving glyceryl monostearate into the various types of vitamin E?

None of the above references have attempted to answer these questions because no one was aware of the potential of the solution formed by dissolving glyceryl monostearate into vitamin E. This application attempts to point out, for the first time, a few of the many potentials of this solution.

This far, glyceryl monostearate and vitamin E were combined into a single solution because the resulting solution was a stepping stone to another product. The present invention explores the potentials of the stepping stone. In addition, this invention describes the stepping stone as a substitute for Vaseline in the field of sexual lubricants. Finally, this invention describes how to prepare a substitute for petrolatum from two such unlikely ingredients as glyceryl monostearate and vitamin E.

SUMMARY OF THE INVENTION

The primary goal in this invention is to find a substitute for Vaseline as a sexual lubricant. The biggest problem with such a preparation is determining which ingredients can safely be incorporated into such a formulation. Very few cosmetic materials are non-toxic and completely free of one danger or another. At first glance, a novice might pick a vegetable oil base or a petrolatum base. However, vegetable oils turn rancid, and petrolatum is not absorbable and is also not biodegradable. Petrolatum tends to collect within a woman. Thus, the solution is not as simple as it first seems. The ideal lubricant is one that is quickly absorbed by the body. Vitamin E is easily absorbed by the body, and it is also non-toxic. However, vitamin E is a thick, viscous, sticky oil. The important point is that it is an oil, and oils tend to thin out. Thus, oils are inadequate lubricants. Petrolatum or Vaseline can be applied in thick, lasting layers. Petrolatum does not flow into such a thin layer that it loses its ability to lubricate. Dissolving 14 parts by weight of glyceryl monostearate into 86 parts by weight of alpha tocopherol acetate produces a solution that comes close to duplicating the properties of Vaseline at room temperature. There are many possible mixtures of the different types of glyceryl monostearate and many different types of vitamin E solutions. This invention describes some of the guidelines that have to be considered in order to prepare a substitute for Vaseline from glyceryl monostearate and vitamin E. That which follows describes some of the conditions that determine some of the different types of hardened vitamin E that can be used as a substitute for Vaseline.

DESCRIPTION OF THE PREFERRED EMBODIMENT

The essence of this invention satisfies the need to duplicant Vaseline, or semisolid petrolatum, with a composition that is more suitable than Vaseline as a sexual lubricant, because it does not suffer from the disadvantages of Vaseline and does resemble Vaseline. In addition, this substitute for Vaseline must be capable of functioning in most of the ways that Vaseline functions.

The herein described invention can substitute for Vaseline in the following ways:
1. It looks and feels like Vaseline.
2. It lubricates like Vaseline.
3. It can be applied in thick protective layers that do not flow into thin layers like vegetable oils.
4. It should not break down into dangerous by-products.

The primary disadvantage of Vaseline is created by the fact that Vaseline is not absorbable once it is placed within the vagina and uterus. Thus, Vaseline tends to collect within the female's reproductive system and thereby create severe problems for many women.

This invention circumvents these problems by creating a lubricant that is absorbable and biodegradable. It does this by creating a lubricant that has more than 50% vitamin E. (Most of the following formulations have more than 80% vitamin E in their composition.) Vitamin E is absorbed into surrounding tissues. Thus, vitamin E will not collect within the female reproductive system. Unfortunately, pure vitamin E is a thick oil that is unsuitable as a sexual lubricant. However, dissolving suitable concentrations and suitable types of glyceryl monostearate into vitamin E will produce a solution that resembles solid petrolatum (Vaseline) provided the right type of vitamin E is used.

Appropriate mixtures of glyceryl monostearate and vitamin E can be improved upon by adding vegetable oil provided that it is protected from oxidation. This precaution is necessary, because rancid oils are highly toxic. Considering the sensitivity of the reproductive system, it is advisable to avoid the use of vegetable and seed oils. Jojoba oil is a suitable oil to substitute for vegetable oils, because it resists oxidation. Some of the following formulations include jojoba oil.

The following examples illustrate the invention in greater detail. In these examples, proportions of ingredients are expressed as parts by weight. The flow points, or the temperature at which a melted formulation will stop flowing, is given in degrees Fahrenheit. Other descriptive facts are also included to describe the factors that must be considered in the search for a substitute for Vaseline, or solid petrolatum.

The flow point for Vaseline is 115 degrees Fahrenheit. However, it is the physical properties that have to be duplicated, not the flow temperature alone.

Possible Formulations Involving the Use of Pure Glyceryl Monostearate and Alpha Tocopherol Acetate (D L) USP G.M.S. is the abbreviation for glyceryl monostearate (pure).
A.T.A. is the abbreviation for Alpha Tocopherol Acetate.
Soya oil is included for comparison purposes mainly.

| Formula | G.M.S. | A.T.A. | Jojoba Oil | Soya Oil | Flow Point |
|---|---|---|---|---|---|
| 1 | 33.3 | 66.6 | 0 | 0 | 118 |
| 2 | 33.3 | 33.3 | 33.3 | 0 | 120 |
| 3 | 33.3 | 33.3 | 0 | 33.3 | 122 |
| 4 | 25 | 75 | 0 | 0 | 113 |
| 5 | 25 | 50 | 25 | 0 | 116 |
| 6 | 20 | 80 | 0 | 0 | 113 |
| 7 | 20 | 60 | 20 | 0 | 114 |
| 8 | 20 | 60 | 0 | 20 | 113 |
| 9 | 16.6 | 83.4 | 0 | 0 | 105 |
| 10 | 16.6 | 66.4 | 16.6 | 0 | 105 |
| 11 | 16.6 | 66.4 | 0 | 16.6 | 95 |
| 12 | 14.5 | 85.5 | 0 | 0 | 95 |

Formula number 12 is most like Vaseline. Formula number 9 also is quite like Vaseline, but a little stiff and a little less effective as a lubricant. Formula number 10 is an adequate lubricant because of the presence of jojoba oil. Formula number 1 is very thick and is much harder to apply than Vaseline. However, vaseline has other functions. Vaseline can be used as a carrier to suspend a large variety of medications and antibacterial agents. Formula 1 might function as a carrier for medication. Higher concentrations of glyceryl monostearate will result in a solid solution that can be used as a stick cosmetic. For example, a solid solution containing 50% G.M.S. and 50% A.T.A. can still be spread on the human skil especially if a small amount of jojoba oil is incorporated into the formulation.

The Effect of Using Pure Alpha Tocopherol and Pure Glyceryl Monostearate

A.T. refers to Alpha Tocopherol. The proportions are in parts by weight

| Formula | Pure G.M.S. | A.T. | Jojoba Oil | Flow Temperature (degrees F.) | Comments |
|---|---|---|---|---|---|
| 13 | 25 | 75 | 0 | 80 | Compare with 4 |
| 14 | 40 | 60 | 0 | 100 | Compare with 1 |
| 15 | 33.3 | 66.6 | 0 | 90 | Compare with 1 |

Formula 13 is much softer than formula 4. Formula 15 is also much softer than formula 1. Conclusion: Alpha tocopherol acetate requires less pure glyceryl monostearate to harden it than alpha tocopherol. Alpha tocopherol acetate is also more resistant to oxidation. Thus, alpha tocopherol acetate is preferred over alpha tocopherol, because we can prepare a substitute for Vaseline from it that uses less glyceryl monostearate. This is good because it is the vitamin E that is absorbable. This is one reason why formula 12 is so good; 85% of formula 12 is absorbable. This is much beter than Vaseline because zero percent of Vaseline is absorbable. However, there may be medical reasons for preferring alpha tocopherol. In this case, a formulation that contains 33% pure glyceryl monostearate may have to be used.

The Effect of Glyceryl Monostearate (Acid Stable) and Glyceryl Monostearate (Self-Emulsifying) on Alpha Tocopherol Acetate Acid stable means that the G.M.S. has polyethylene glycol 300 incorporated into the crystals of solid G.M.S. The manufacturer states that there is close to 50% polyethylene glycol mixed into the glyceryl monostearate. Self-emulsifying means that potassium stearate is incorporated into the G.M.S.

| Formula | G.M.S. Acid Stable | G.M.S. Self-Emulsifying | A.T.A. | A.T. | Flow Temperature |
|---|---|---|---|---|---|
| 16 | 25 | | 75 | | 102 |
| 17 | 25 | | | 75 | 85 |
| 18 | | 25 | 75 | | 90 |
| 19 | 40 | | 60 | | 115 |

Conclusions: comparing formulas 4 with 18 and 16 we conclude that self-emulsifying G.M.S. has the least ability to raise the flow temperature of A.T.A. In addition, pure G.M.S. has the greatest ability to raise the flow temperature of solutions that contain G.M.S. and alpha tocopherol acetate. This means that pure G.M.S. will produce hardened vitamin E that has the lowest concentration of glyceryl monostearate.

Consider the following:

| Formula | G.M.S. Pure | G.M.S. Self-Emulsifying | A.T.A. | Flow Temperature |
|---|---|---|---|---|
| 20 | 11.5 | 11.5 | 77 | 90 |

Conclusions: The flow point can be lowered by adding G.M.S. self-emulsifying.

The Effect of G.M.S. Acid Stable and G.M.S. Self-Emulsifying on Solutions Made With Alpha Tocopherol (No Acetate)

| Formula | Acid Stable G.M.A. | Self-Emulsifying G.M.S. | Alpha Tocopherol | Flow Temperature |
|---|---|---|---|---|
| 21 | 25 | 0 | 75 | 75 |
| 22 | 33.3 | | 66.6 | 85 |
| 23 | | 25 | 75 | 70 |
| 24 | | 33.3 | 66.6 | 80 |
| 25 | | 40 | 60 | 90 |
| 26 | 40 | | 60 | 98 |

Conclusions: The acid stable glyceryl monostearate produced a soft and pliable product even at 40% concentrations. Thus, formula number 26 is softer and more pliable than formula 25. Formula 25 is hard enough to be used as a stick cosmetic. Formula 6, above, is only slightly more stiff than Vaseline and is certainly not hard enough to be used as a stick cosmetic. However, its flow temperature is 113. Thus, the different forms of glyceryl monostearate do have a different effect on the physical characteristics of the solutions discribed above, and the flow temperatures or melting points do not paint the entire picture. For example, the acid stable formulations are more transparent. Vaseline also has a transparent quality. Thus, formulations that contain acid stable glycerol monostearate more closely resembly Vaseline. All other formulations are more translucent even though they may resemble Vaseline in every other way. Formula 12 is the closest physically to Vaseline, despite the fact that its flow temperature is 95 degrees Fahrenheit. However, all of the above formulas have potential as a substitute for Vaseline. Polyethylene glycol is the ingredient that makes acid stable G.M.S. an effective additive to the above formulations. Its presence seems to make G.M.S. more soluable in vitamin E.

However, a solution that contains 20% G.M.S. acid stable and 80% alpha tocopherol acetate forms a thick cohesive solution that does not resemble Vaseline or solid petrolatum. Reducing the concentration of G.M.S. acid stable and adding jojoba oil reduces the cohesive force and produces a solution that is less sticky and more of a lubricant. Other forms of G.M.S. can replace G.M.S. acid stable. The formulation that involves these four ingredients is:

| Formula | Acid Stable G.M.S. | Pure G.M.S. | A.T.A. | Jojoba Oil | Flow Point |
|---|---|---|---|---|---|
| 27 | 12.5 | 12.5 | 62.5 | 12.5 | 105 |

Formula 27 is a possible substitute for Vaseline.

Some of the other properties and potentials of the various forms of G.M.S. can be brought out by describing their effect on the mixed tocopherols. The mixed tocopherols contain D alpha, D beta, D gamma and D delta tocopherols. These mixtures are extracted from natural oils and are usually available in concentrated oil solutions. The following formulas are based on a solution containing 70% vitamin E and 30% vegetable oil.

| Formula | Pure G.M.S. | Acid Stable G.M.S. | Self-Emulsifying G.M.S. | 70% Mixed Tocopherols | Flow Temperature |
|---|---|---|---|---|---|
| 28 | | | 33.3 | 66.6 | 90 |
| 29 | | 33.3 | | 66.6 | 75 |
| 30 | 33.3 | | | 66.6 | 90 |

When using mixed tocopherols, the acid stable G.M.S. has less effect on the flow temperature then the other forms of G.M.S. Formulas 28 and 30 do not duplicate petrolatum as effectively as formula 29. Formula 29 is soft, translucent and spreadable, and is a lubricant that resembles petrolatum (Vaseline). In addition, formula 29 is crystal clear when it is melted. As a matter of fact, the only formulas that are crystal clear in the melted state are those that have some acid stable G.M.S. This is an indication that polyethylene glycol somehow assists the solution of G.M.S. into vitamin E and that such solution is important to duplicating Vaseline's physical characteristics.

Formulas 9 and 14 are simpler formulations that can substitute for Vaseline. There is nothing in 9 and 14 that can cause adverse reactions within a woman's reproductive system and more than 80% of 9 and 14 can be absorbed as vitamin E. The Handbook of Cosmetic Materials states that the carbowaxes have not been approved for internal use. Thus, it is not known whether such a compound can be used as a part of a sexual lubricant. Ultra-conservative formulas such as 9 and 14 may prove to be the ones that win wide approval in the end because 80% to 85% of them is absorbable in the form of vitamin E. The remainder is G.M.S., a chemically stable and otherwise innocuous, biodegradable compound. Alpha tocopherol acetate is the most suitable form of vitamin E to use in the invention, because it is the most resistant to oxidation, and because its formulation requires less glyceryl monostearate. Glyceryl monostearate pure is the best, because its formulas have less glyceryl monostearate. Compare 4, 16 and 18.

I claim:

1. A nontoxic sexual lubricant, which resembles solid petrolatum, prepared by combining from 12.5 to 25 parts by weight of glyceryl monostearate pure with from 50 to 66.4 parts by weight of alpha tocopherol acetate to form a solution with the aid of heat and thereafter incorporating from 12.5 to 25 parts by weight of jojoba oil to yield a mixture which is solid at room temperature.

2. A nontoxic sexual lubricant as recited in claim 1, wherein 12.5 to 16.6 parts by weight of said glyceryl monostearate pure are combined with from 62.5 to 66.4 parts by weight of said alpha tocopherol acetate to form said solution with the aid of heat and wherein thereafter 12.5 to 16.6 parts by weight of said jojoba oil are incorporated in said solution to yield said mixture which is solid at room temperature.

* * * * *